United States Patent
Cuzzato et al.

(10) Patent No.: US 6,323,379 B1
(45) Date of Patent: Nov. 27, 2001

(54) PROCESS FOR OBTAINING PENTAFLUOROETHANE BY TETRAFLUOROCHLOROETHANE DISMUTATION

(75) Inventors: Paolo Cuzzato, Treviso; Letanzio Bragante; Francesco Rinaldi, both of Padova, all of (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/568,594

(22) Filed: May 11, 2000

(30) Foreign Application Priority Data

May 13, 1999 (IT) .............................................. MI99A1037

(51) Int. Cl.⁷ ................................................... C07C 19/08
(52) U.S. Cl. .......................................... 570/163; 570/151
(58) Field of Search ...................... 570/151, 163

(56) References Cited

U.S. PATENT DOCUMENTS 4,129,603 * 12/1978 Bell ...................................... 570/151
5,345,014    9/1994 Cuzzato .

FOREIGN PATENT DOCUMENTS

| 117 444 | 1/1976 | (DE) . |
| 0 130 532 A2 | 1/1985 | (EP) . |
| 0 408 005 B1 | 1/1991 | (EP) . |
| 0 569 832 A1 | 11/1993 | (EP) . |
| 0 776 878 A2 | 6/1997 | (EP) . |
| 1383927 | 11/1963 | (FR) . |

* cited by examiner

Primary Examiner—Alan Siegel
(74) Attorney, Agent, or Firm—Arent Fox Kintner Plotkin & Kahn, PLLC

(57) ABSTRACT

A process for obtaining pentafluoroethane HFC 125 by dismutation of gaseous tetrafluorochloroethane HCFC 124, at temperatures in the range 200°–300° C., on a trivalent chromium oxide ($Cr_2O_3$) catalyst, supported on aluminum fluoride, by feeding HF in such amount that the HCFC 124/HF molar ratio is in the range 10/1–1/1.

11 Claims, No Drawings

PROCESS FOR OBTAINING PENTAFLUOROETHANE BY TETRAFLUOROCHLOROETHANE DISMUTATION

The present invention relates to a process which allows to obtain in high yields very pure $CHF_2$—$CF_3$ (HFC 125).

HFC 125 is an harmless fluorocarbon for the ozone layer, therefore meeting the requirements of the Montreal Treaty. For the commercial uses of the compound an high purity is required.

The possibility to obtain pure pentafluoroethane depends on the type of impurities which are formed during the synthesis. For example CFC 115 (chloropentafluoroethane $CF_2Cl$—$CF_3$) is an impurity which can be eliminated with difficult from HFC 125, therefore its presence does not allow to obtain the compound at a very pure level. In order to produce pentafluoroethane meeting these requirements, processes must be employed wherein CFC 115 does not form or is formed only in traces.

The processes used in the prior art to obtain HFC 125 do not allow to obtain the compound in high yield and purity. In U.S. Pat. No. 5,345,014 in the name of the Applicant HFC 125 is obtained by a dismutation reaction of gaseous HCFC-124 (tetrafluorochloroethane $C_2HF_4Cl$) in the presence of supported $Cr_2O_3$, at temperatures in the range 150°–330° C., for contact times between 1 and 20 seconds. A mixture of HFC 125, HCFC 115 and 2,2-dichloro, 1,1,1-trifluoroethane $CF_3$—$CHCl_2$ (HCFC-123), together with lower amounts of other by-products, is formed. Tests carried out by the Applicant have shown that by this process it is not possible to combine an high yield in HFC 125, calculated as molar ratio between the obtained HFC 125/reacted HCFC 124, with the purity required for the product, since by using reaction conditions such as to increase the yield in HFC 125, at the same time also CFC 115 increases. It has been furthermore verified that the product obtained with the process according to this patent contains also impurities of dichlorotetrafluoroethane and of $C_2F_4Cl_2$ isomers. Besides it is to be considered that the starting compound HCFC 124 contains CFC 114 which is an impurity difficult to be separated since it has an high affinity towards HCFC 124 and when the unreacted tetrafluorochloroethane is recycled, in the reaction conditions CFC 114 can dismutate forming CFC 115.

In the European patent application EP 776,878 in the name of the Applicant a process for preparing pentafluoroethane with very low residual amounts of CFC 115, is described. The compound is obtained by dismutation in gaseous phase of tetrafluorochloroethane $CF_3CHClF$ (HCFC 124) to form HFC 125 and HCFC 123, in the presence of a catalyst formed of chromium oxide $Cr_2O_3$ supported on $AlF_3$, for contact times between 15 and 30 seconds at temperatures in the range 140° C.–180° C. The contact times decrease up to 0.1–1 seconds at temperatures in the range 260° C.–300° C. The Examples show that the CFC 115 amount is very low and in some cases negligible, but the yield in HFC 125 is unsatisfactory and the molar ratio HFC 125/HCFC 123 is always very close to the unit.

The need was felt to prepare HFC 125 substantially impurity-free, specifically CFC 115, with a combination of an improved yield and purity with respect to the prior art.

The solution of these technical problems has been reached by the process as described hereinbelow.

An object of the present invention is a process wherein pentafluoroethane HFC 125 is obtained by dismutation of gaseous tetrafluorochloroethane HCFC 124, at temperatures in the range 200° C.–300° C., preferably 250° C.–280° C. on a trivalent chromium oxide ($Cr_2O_3$) catalyst, preferably supported, preferably the support is aluminum fluoride, feeding a HF amount such that the HCFC 124/HF molar ratio is comprised in the range 10/1–1/1, preferably 2/1–1/1.

The contact time with the catalyst, determined as the ratio between the catalyst volume and that of the gas flow at the working temperature and pressure, is in the range 1–50 seconds, preferably 5–30 seconds.

The pressure is not critical, one commonly works at atmospheric pressure (1 atm) or higher. For example one can operate at pressures up to 5 atm or higher.

In the process optionally inert gases, such as for example nitrogen, as diluents of the reaction gases, can be used.

The supported catalyst is prepared by using a chromium chloride solution and an aluminum fluoride support, usually with the method known as "dry impregnation", for example as described in EP 408,005, herein incorporated by reference.

At the end of the impregnation, the catalyst must be activated: the operation can be directly carried out in the reactor used for the dismutation, by calcining in inert gas current, at the temperature of about 400° C. for 4–8 hours and then by treating at 360° C. with anhydrous HF for 12–24 hours.

The aluminum fluoride used as a support is obtainable by alumina fluorination, and it has a fluorine content not lower than 90%, preferably not lower than 95%, with respect to the stoichiometric.

Generally the $AlF_3$ is mainly formed of gamma phase, as described in FR 1,383,927, and has a surface area generally in the range 25–35 m$^2$/g. If the catalyst is used in a fluidized bed the support has the granulometry suitable for this kind of reactor, as well known to the skilled in the art. The chromium content in the supported catalyst is in the range 1–15% by weight.

According to the process object of the present invention it is possible to increase the yield, calculated as molar ratio between the obtained HFC 125/reacted HCFC 124, up to 70% and more, maintaining weight ratios CFC 115/HFC 125 and CFC 114/HCFC 124 lower than or equal to 1000 ppm.

The reaction is preferably carried out in a continuous way and the catalyst is used in a fluidized bed.

The following Examples illustrate the invention and do not limit the scope thereof.

EXAMPLE 1a

Catalyst Preparation

The catalyst for fluidized bed was prepared by impregnating $AlF_3$ in granules with an aqueous solution containing $CrCl_3.6H_2O$, in weight ratio 0.492:1 chromium salt:$AlF_3$, by means of the dry impregnation method described in EP 408.005.

$AlF_3$, mainly in gamma form and having a specific surface area of 26 m$^2$/g, was impregnated with a $CrCl_3.6H_2O$ aqueous solution in an amount equal to 492 g of the salt/Kg of $AlF_3$.

The solution consisting of 492 g of the chromium chloride hexahydrate dissolved in 152 ml of water has a volume of 450 ml and was added to $AlF_3$ (1 Kg) in 3 nearly equal portions. After each addition, the catalyst is dried for 4 hours at 120° C. at atmospheric pressure. The catalyst at last is sieved and transferred in a tubular reactor to be activated. The activation is carried out by letting flow through the reactor first a nitrogen flow for 10 hours at 400° C. then an ahydrous HF flow at a temperature not lower than 350° C., for 24 hours.

The final chromium content in the catalyst is 8% by weight.

EXAMPLE 1b

Commparative Process According to the Prior Art (U.S. Pat. No. 5,345,014)—Dismutation of HCFC 124 at a Temperature in the Range 150° C.–330° C.

300 ml of catalyst prepared in the Example 1a, corresponding to 390 g, are fed to a tubular Inconel reactor, 50 mm diameter, equipped with an electric heating, in which a temperature of 280° C. is maintained. The HCFC 124 feeding is 185 g/h, corresponding to 1.36 moles/h and the contact time is 18 s.

The gases flowing out from the reactor are let bubble in water to remove HCl and possible HF traces, then analyzed by gaschromatography. Samples are taken at the following times calculated from the beginning of the reacting gas flow in the reactor: 5.5, 22 and 46.5 hours. The percentages of the mixture components are expressed as % by moles. The results are reported in Table I.

The HFC 125/HCFC 123 molar ratio is on an average slightly lower than 2, and the weight ratios CFC 115/HFC 125 and CFC 114/HCFC 124 are high, of the per cent unit order. The unreacted HCFC 124 is recycled.

In Table III the yield in HFC 125, calculated as molar ratio HFC 125/reacted HCFC 124, is reported, which has an average value of 63%.

EXAMPLE 1c

Reaction of HCFC 124 with HF According to the Invention

After 70 hours of running an HF flow of 20 g/h (1.0 moles/h) is added. The HCFC 124/HF molar ratio is 1.36:1. The analyses are effected on samples taken at 72, 90.5, 94.5, 98.5 hours. The results are reported in Table II.

From Tables I and II it results that in the process according to the present invention, in comparison with that carried out according to the prior art, the HFC 125/HCFC 123 molar ratio increases on an average from 2.1 to 2.9, and that at the same time the weight ratios CFC 115/HFC 125 and CFC 114/HCFC 124 decrease.

From Table III it results that the yield in HFC 125 defined as HFC 125 moles/converted HCFC 124 moles, is substantially improved in comparison with that obtained in the process described in the previous comparative Example 1b.

The balance of the useful products is clearly favourable in the Example 1c according to the present invention, since HCFC 124 is completely recyclable to the reactor and the HCFC 123 amounts are reduced, on an average of 3.5 times lower than those of Example 1b. In a continuous industrial process this represents a remarkable advantage. 2,2-dichloro, 1,1,1,-trifluoroethane $CF_3$—$CHCl_2$ cannot be recycled as such, wherefore it must be disposed or reused in another form, for example by transforming it in another fluorocarbon reusable in the process. In the Example 1b according to the prior art, as said, there are remarkable amounts of 123.

TABLE I

Ex. 1b comp.: dismutation reaction of HCFC 124 according to the prior art (U.S. Pat. No. 5,345,014)

| Time from the beginning of the gas flow to the reactor | Main products (% by moles) | | | 115/125 % by weight | 114/124 % by weight |
|---|---|---|---|---|---|
| (hours) | 125 | 124 | 123 | | |
| 5.5 | 47.7 | 24.5 | 25.0 | 2.2 | 2.4 |
| 22 | 45.6 | 26.4 | 23.1 | 1.1 | 2.1 |
| 46.5 | 49.3 | 21.7 | 22.7 | 1.5 | 2.5 |

TABLE II

Ex. 1c: dismutation reaction of HCFC 124 according to the invention

| Time from the reaction beginning | Main products (% by moles) | | | 115/125 % by weight | 114/124 % by weight |
|---|---|---|---|---|---|
| (hours) | 125 | 124 | 123 | | |
| 72 | 19.3 | 71.6 | 7.9 | n.d.* | 0.1 |
| 90.5 | 19.5 | 73.6 | 6.5 | 0.058 | 0.1 |
| 94.5 | 18.9 | 74.4 | 6.5 | 0.064 | 0.1 |
| 98.5 | 19.3 | 74.5 | 5.9 | 0.058 | 0.1 |

*not detectable

TABLE III

Yield in HFC 125, calculated as molar ratio HFC 125/reacted HCFC 124, at the running times mentioned in Tables I (dismutation reaction according to the prior art) and II (process according to the present invention) respectively

| Ref. Table | Time from the reaction beginning (h) | Yield % ratio by moles 125/reacted 124 |
|---|---|---|
| Table I | 5.5 | 63 |
| | 22 | 62 |
| | 46.5 | 63 |
| Table II | 72 | 68 |
| | 90.5 | 74 |
| | 94.5 | 74 |
| | 98.5 | 75 |

What is claimed:

1. A process for obtaining pentafluoroethane HFC 125 by dismutation of gaseous tetrafluorochloroethane HCFC 124, at temperatures in the range 200° C.–300° C., on a trivalent chromium oxide ($Cr_2O_3$) catalyst, optionally supported, by feeding an HF amount such that the HCFC 124/HF molar ratio is in the range 10/1–1/1.

2. A process according to claim 1, wherein the temperature is in the range 250° C.–280° C.

3. A process according to claim 1, wherein the contact time with the catalyst is in the range 1–50 seconds.

4. A process according to claim 1, wherein the aluminum fluoride support is obtainable by fluorination of alumina, and it has a fluorine content not lower than 90%, with respect to the stoichiometric.

5. A process according to claim 4, wherein the aluminum fluoride is mainly constituted by gamma phase, and has a surface area in the range 25–35 $m^2/g$.

6. A process according to claim 1, wherein the chromium content in the supported catalyst is in the range 1–15% by weight.

7. A process according to claim 1, carried out in a fluidized bed.

8. A process according to claim 1, wherein the catalyst is supported on aluminum fluoride.

9. A process according to claim 1, wherein the HCFC 124/HF molar ratio is in the range 2/1–1/1.

10. A process according to claim 3, wherein the contact time with the catalyst is in the range 5–30 seconds.

11. A process according to claim 4, wherein the aluminum fluoride support has a fluorine content not lower than 95%.

* * * * *